United States Patent [19]

Srivastava et al.

[11] Patent Number: 4,813,588

[45] Date of Patent: Mar. 21, 1989

[54] INSPECTION AND REPAIR OF TAB LIFTED LEADS

[75] Inventors: Nilendu Srivastava; Fei-Jain Wu, both of Chelmsford, Mass.

[73] Assignee: Technical Manufacturing Corporation, Peabody, Mass.

[21] Appl. No.: 101,189

[22] Filed: Sep. 25, 1987

[51] Int. Cl.⁴ .................. B23K 37/00; G02B 21/06
[52] U.S. Cl. ........................... 228/103; 228/105; 228/179; 228/6.2; 228/44.7; 228/119; 350/523; 29/833
[58] Field of Search ............... 228/103, 105, 179, 6.2, 228/44.7, 119; 350/523–527; 29/833

[56] References Cited

U.S. PATENT DOCUMENTS

| | | | |
|---|---|---|---|
| 3,724,068 | 4/1973 | Galli | 29/833 |
| 3,730,342 | 5/1973 | Egan et al. | 350/526 |
| 3,982,979 | 9/1976 | Hentz et al. | 228/105 |
| 3,997,100 | 12/1976 | Hofmeister | 228/179 |
| 4,342,090 | 7/1982 | Caccoma et al. | 228/180.2 |
| 4,671,446 | 6/1987 | Sherman | 228/179 |

FOREIGN PATENT DOCUMENTS

| | | | |
|---|---|---|---|
| 2503860 | 10/1982 | France | 228/105 |
| 157588 | 9/1983 | Japan | 228/105 |
| 293657 | 12/1986 | Japan | 228/103 |

Primary Examiner—Nicholas P. Godici
Assistant Examiner—Samuel M. Heinrich
Attorney, Agent, or Firm—Samuels, Gauthier Stevens & Kehoe

[57] ABSTRACT

An optical video system for the inspection and repair of TAB lifted leads. Three distinct light sources are aligned at different angles to illuminate the side of a lead-solder-pad joint. Each of the surfaces of the joint are readily distinguished.

20 Claims, 5 Drawing Sheets

INSPECTION AND REPAIR OF TAB LIFTED LEADS

BACKGROUND AND BRIEF SUMMARY OF THE INVENTION

A tape automated bonding (TAB) package consists of bonding a large chip bonded to metal foils. The conductive pads at the edge of the package are attached by soldering, welding or conductive epoxying to the printed circuit boards or substrates. The bonding of the pads (leads) of the metal foil to the chip is known as inner lead bonding (ILB) and the bonding of the pads (leads) to the printed circuit boards or substrate matching pads is known as outer lead bonding (OLB).

Though tape automated bonding has been in existence for about two decades, the prime thrust as yet has been on low lead count (less than 100 leads, typically 16 to 32 leads) TAB devices. The recent technological development in VLSI chips with denser Input/Output and surface mounting of packages with finer lead pitch has generated tremendous interest in high lead count (200+leads) TAB packages. As the number of leads on TAB devices is increasing, the pitch (distance between the center lines of two adjoining leads) is getting smaller. This poses new challenges to the manufacturing, testing, reliability, performance, etc. of such packages.

The present invention is directed to an apparatus and a method for inspecting outer lead bond joints for lifted leads and for repairing them in situ. It is within the scope of this invention to extend the technique to inner lead bonds and similar tasks.

After TAB devices are aligned and bonded to the corresponding pads of the substrates, many times cold solder joints or solder failures occur. This is due to the fact that the bonding head does not apply enough pressure or even pressure on all leads and/or due to the fact that enough heat is not transferred to the leads and to the solder to form a good bond. Such conditions are referred to as lifted leads. In the case of a cold solder joint, a narrow break or fissure appears either between the lead and solder or between the solder and pad due to lack of solder reflow. A solder failure means there is no bond between the lead and the pad which, again, is due to the lack of solder reflow. Typically, this will create air gaps in between the lead and pad but, in some cases, it can also end up with no air gaps.

Existing visual techniques for either inspecting or repairing lifted leads of TAB devices are generally unsatisfactory. The known inspection systems have failed to inspect lifted leads because of their inability to either identify the lifted leads or to differentiate between a good and a lifted lead.

Generally, in high lead count TAB devices the width of the lead-pad may be in the order of a few to several mils. The effective length of the outer lead bond may be in the order of 20 to 80 mils. When the joints (lead-solder-pad combination) are viewed under high power magnification, from the top, generally with a collimated light source, the pad on the PCB (substrate) and the solder underneath are hidden by the TAB lead on the top. Even when viewed from an angle, the dispersion of the light from the surfaces is such that it is difficult to distinguish among the surfaces of the lead, the solder and the pad. Further, where a lead is not soldered properly, the pad may contain solder and solder may also be on the sides or under surface of the lifted lead. Current viewing systems have difficulty distinguishing among these surfaces.

Broadly, the invention comprises a plurality of light sources adapted to illuminate at least one TAB joint which comprises a first light source of collimated light disposed above and in front of the sides of the surfaces of the joint under investigation; a second source of fluorescent light disposed above and behind the joint; and a third source of fiber optic light, said fiber optic light comprising at least two bundles whereby two beams of fiber optic light illuminate the sides from a third angle(s). The angular relationship of the light sources illuminating the respective sides of the surfaces of the lead-solder-pad is such that surfaces may be readily distinguished.

DESCRIPTION OF THE PREFERRED EMBODIMENT

Figure 1:
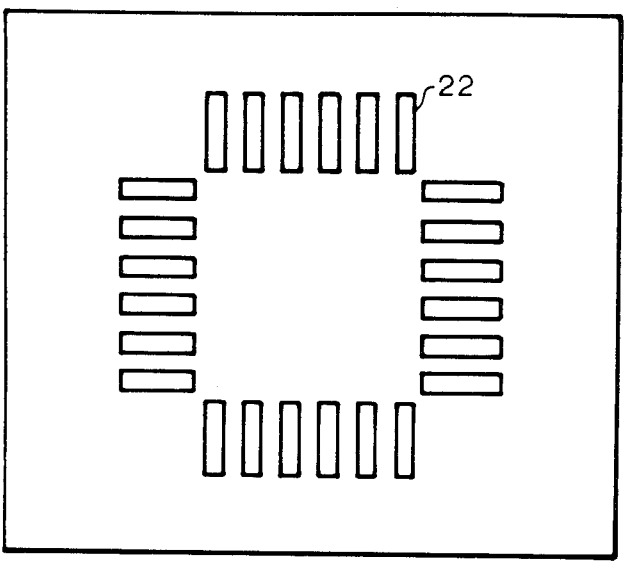
FIG. 1 is a plan view of a substrate before bonding.
Figure 2:
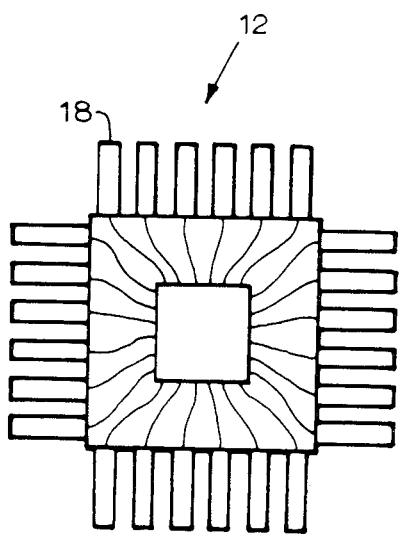
FIG. 2 is a plan view TAB device before bonding to the substrate.
Figure 3:
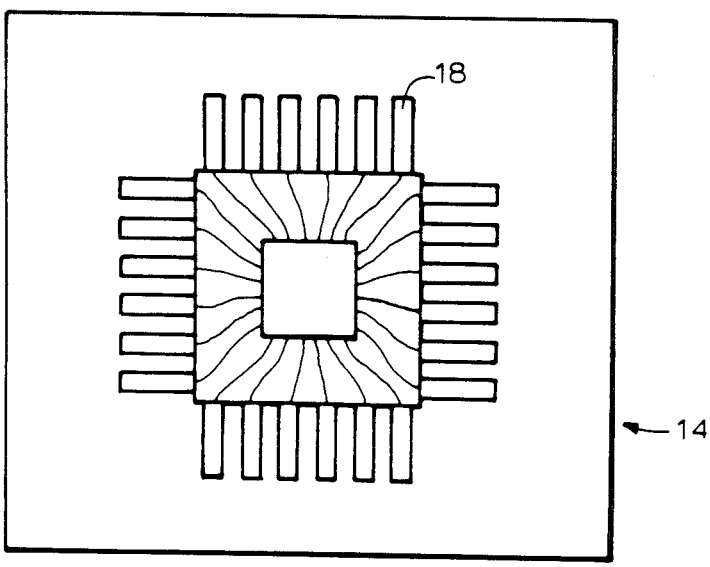
FIG. 3 is a plan view of the TAB bonded to the substrate, pads of substrate are shown longer for clarity.

Referring to FIGS. 1-3, a substrate 10 and a TAB device 12 before bonding are shown. A bonded TAB device 14 is shown in FIG. 3.

Figure 4:
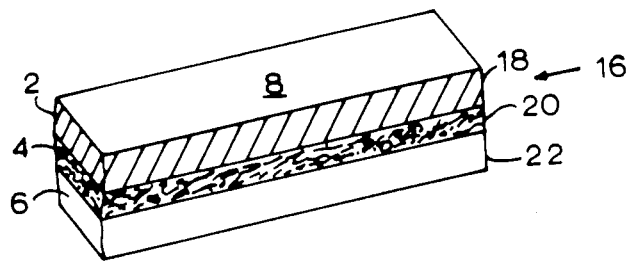
FIG. 4 is a perspective view of a proper bond.
Figure 5:
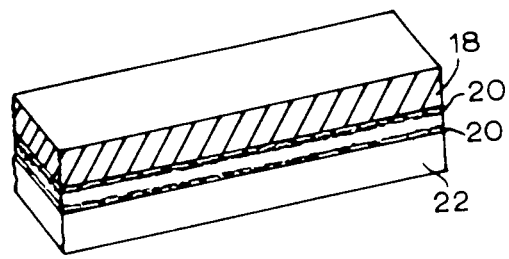
FIG. 5 is a perspective view of an improper bond with a lifted lead.
Figure 6:
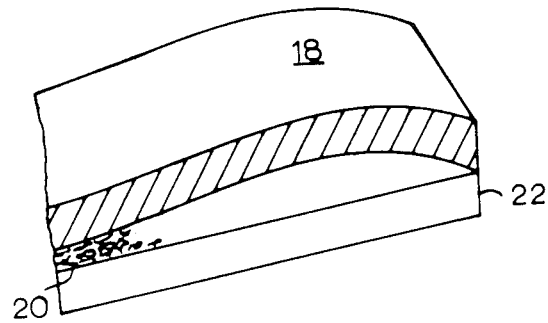
FIG. 6 is a perspective view of an improper bond with a partially lifted lead.
Figure 7:
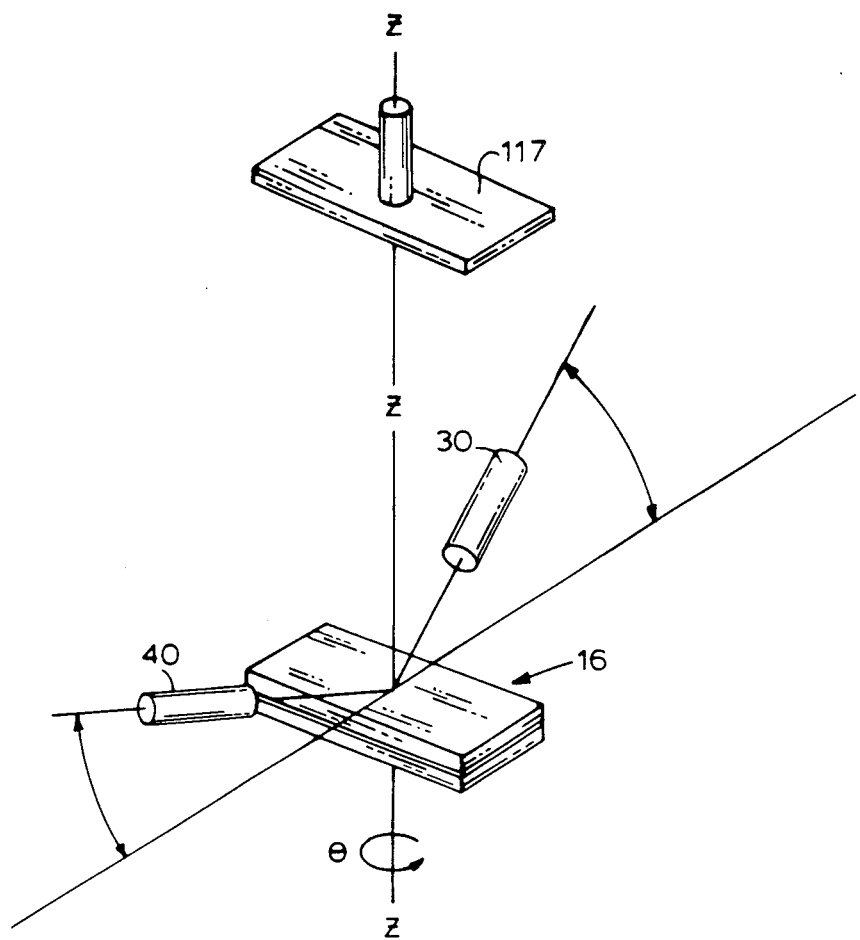
FIG. 7 is a perspective view illustrating the relationship of the collimated and fluorescent light sources.

Referring to FIG. 4, a lead-solder-pad joint 16 is shown properly bonded and comprises a lead 18, solder 20 and a pad 22. This same relationship, lead-solder-pad, is shown in FIGS. 5 and 6 with improper bond, FIG. 5 illustrating a crack or gap and FIG. 6 illustrating a partially lifted lead.

As shown in FIG. 4, each joint 16 has two vertical sides and a vertical end all defining a U-shaped configuration. Each side comprises three distinct surfaces 2, 4 and 6 corresponding to the lead-solder-pad elements of the joint. Distinguishing the three surfaces and viewing them as an integral unit will reveal if there is, in fact, an improperly bonded lead.

In the description of the preferred embodiment, for purposes of illustration, the angular relationships will be described with reference to the lead-solder-pad joints lying on a horizontal plane and the surfaces 2, 4 and 6 which are to be viewed for inspection lying in a vertical plane with reference to horizontal. As will become apparent, it is not necessary that the lead-solder-pad joint lie in a horizontal plane rather it may lie in any plane and the angular relationships to be described will vary accordingly.

Figure 10:
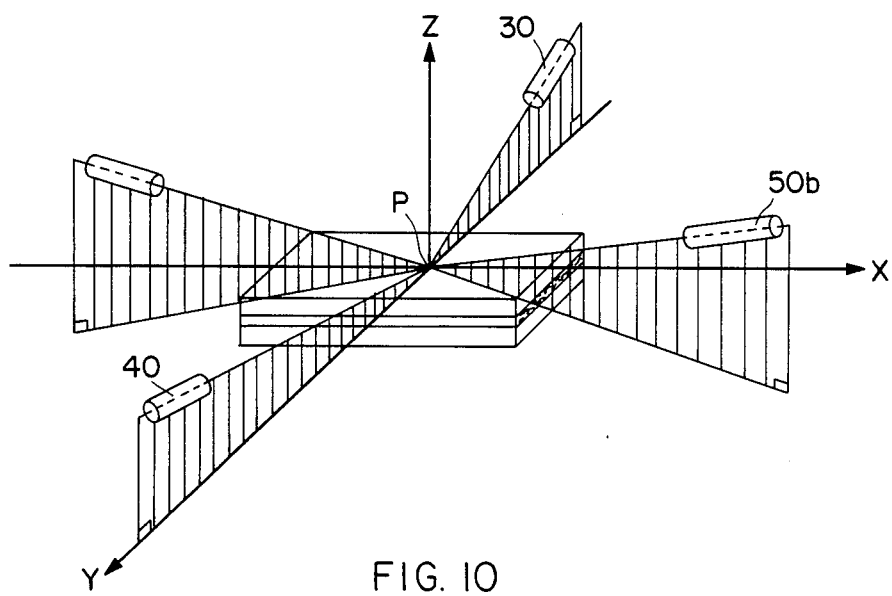
FIG. 10 is a perspective view of the light sources.
Figure 11:
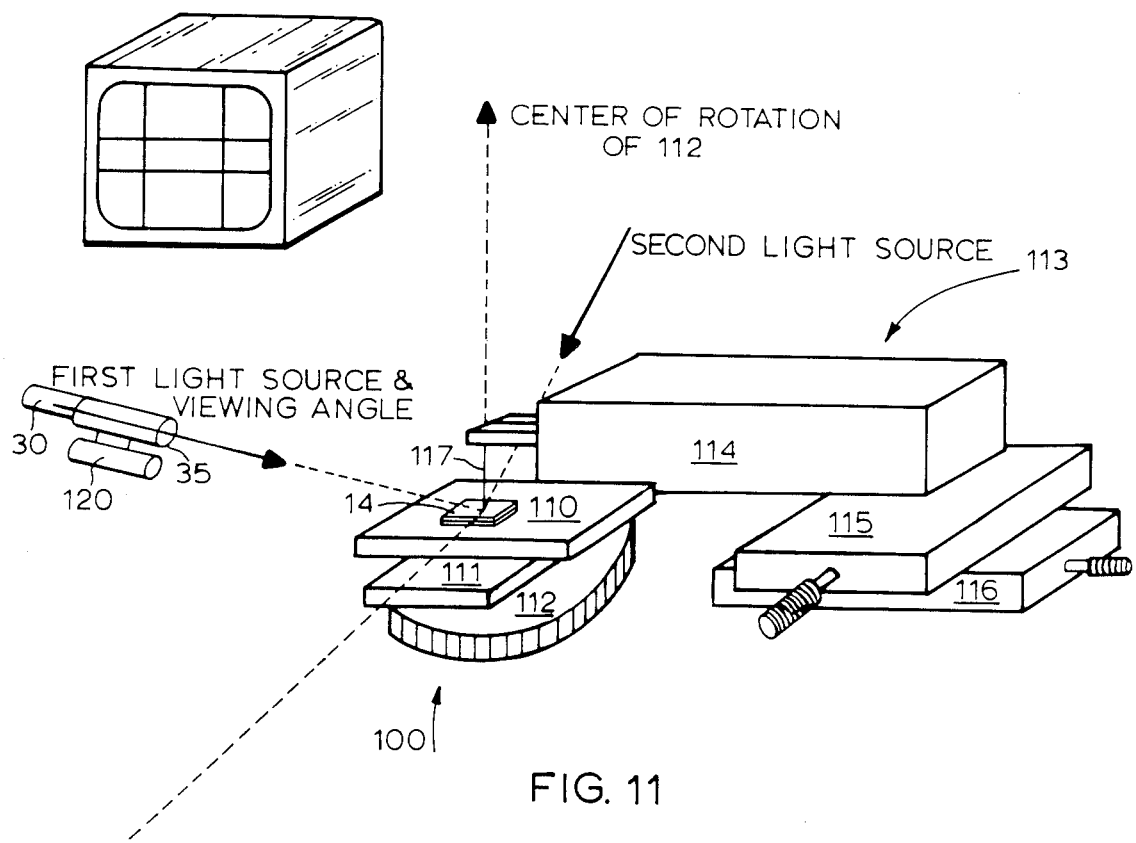
FIG. 11 is an illustration of the system with the TAB mounted on a table, a video display unit and a bonding device.

The bonded TAB device 14 is secured to a table assembly 100, shown in FIG. 11, such as an XY table which allows for linear movement in increments of 0.012 mm in the x and y directions, and rotatable movements in increments of 90° about the z axis. The axes of illumination of the light sources define an area of illumination to view the surfaces under investigation and in the preferred embodiment the axes are located such that they intersect at a common point P. This point is at the approximate center of the top surface of the joint under investigation as shown in FIGS. 7–10. The table 100 is calibrated such that its axis of rotation, z, coincides with the common point P. With this relationship, once one side of the joint has been aligned and viewed, if desired or necessary the other side may be viewed simply by rotating the table 180°.

Referring to FIGS. 7 through 11, the optical system of the preferred embodiment to view the joint comprises a first source of illumination. A stereo microscope 35 with zoom, such as Wild Model M3C, with a collimated light source 30 secured thereto, such as a Wild type 327619 light, illuminates the three surfaces 2, 4 and 6 of the joint at an angle of between 25° to 45° with reference to the horizontal plane on which the joint lies. The axis of the collimated light axis to the surfaces 2, 4 and 6 lie in a plane which plane is substantially normal to the surfaces under investigation.

A second fluorescent light source 40, specifically a Stoker and Yale Light Mite (which includes its own support), illuminates the surfaces from a rearward direction at an angle of between 45° to 65° with reference to the horizontal. This results in a diverging cone of fluorescent light illuminating the top surface 8 of the lead 18. The axis of the inverted cone representing the fluorescent light, as with the collimated light, lies in a plane which plane is substantially normal to the plane in which the surface 2, 4 and 6 being viewed lie.

Preferably, the axes of these two light sources are 90° apart; i.e. the collimated light at 35°; the fluorescent light at 55°; 40°–50° etc.

Figure 8:
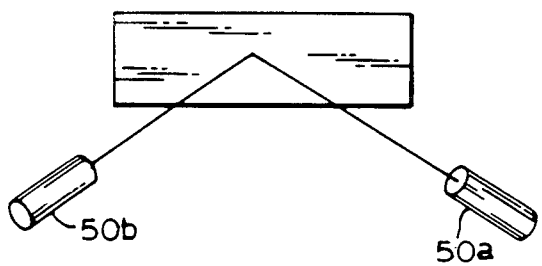
FIG. 8 is a plan view of a third light source of two fiber optics.
Figure 9:
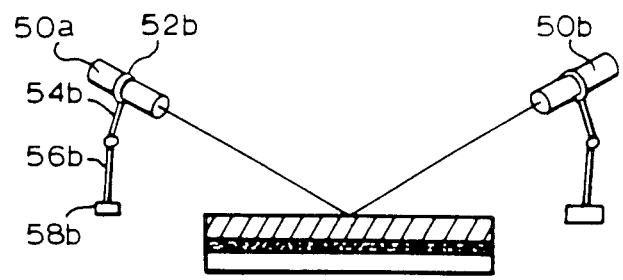
FIG. 9 is a front view of FIG. 8.

The third light source is two fiber optic bundles 50a and 50b shown in FIG. 8 in a plan view. It comprises a Universal 150H light source. The fiber bundles are Dual Fiber Optics bundles 3/16" diameter. The light illuminates the surfaces 2, 4 and 6 at an angle of about 20° to 40°, say for example 30°, with reference to vertical plane in which the surfaces lie. Further, referring to FIG. 9, the fiber optics are also at an angle, with reference to the horizontal plane, of between 20° to 40°, say for example about 30°. The fiber optics may be secured by any structure which will allow their adjustments. For example, they may be clamped for rotary movement at 52b to a link 54b which is pinned to a link 56b which in turn is journaled to a support block 58b. All joints are the type that may be rigidly secured once the final position of the fiber optics is determined. These joints are well known in the art.

Referring to FIG. 10, the optical system is shown in perspective view. It has been found that with the three different types of light sources, in the geometric configuration as described, that three surfaces are each clearly visible such that lifted leads or improperly bonded leads may be readily detected.

In the operation of the invention, after the TAB 14 has been secured to the table assembly, the TAB 14 is viewed with the microscope at midpoint of its depth of field. The microscope is adjusted and/or the table is moved until the best view is attained. The fluorescent light is simply positioned close enough to the joint to ensure the top surface is illuminated. In the preferred embodiment this light source is about 3.5 inches from the joint measured along its axis from point P.

The fiber optic light sources are illuminated and the angles of illumination are adjusted within the ranges described above until, for the particular joint under investigation, a clear distinct view is presented. The fiber optic light sources are then secured in their positions.

The x-y table assembly 100, which is well known in the art, comprises an x-table 100, a y-table 111 and a z-table 112. The bonding assembly 113 comprises a UNITEK 46A weld head 114, with a PM4A Phasemaster 4 Control Unit, and a bonding tip 117.

Each TAB is brought into view for inspection by movement of the table. The joints are moved into the area of illumination successively. This movement can be automated once the initial calibration has been made.

As shown in FIG. 11, a single point bonder 114 is integrated with the system such that the bonding tip 117 may be brought directly onto the TAB joint being inspected. The tip moves up and down in the plane normal to the horizontal plane. When a lifted lead is detected, the bonding head is moved (on linear slides) into position and activated to perform the repair. The bonding head is moved away from the workpiece and the repaired joint can be viewed readily for its integrity. The structure of the bonding unit and its operation are well known in the art.

Figure 12:
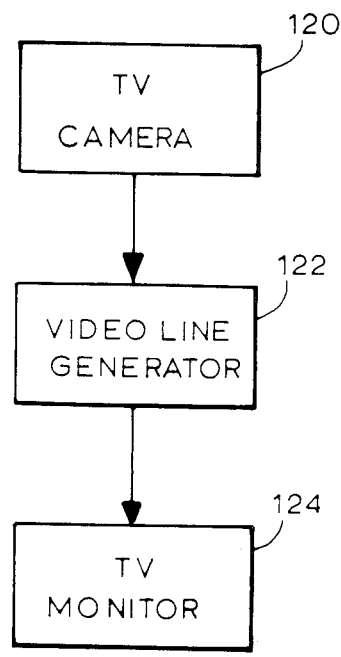
FIG. 12 is a block diagram showing an alternative embodiment of the invention using video display.

In an alternative embodiment, if desired, the input from the microscope can be digitized and displayed on a video terminal as shown in the block diagram in FIG. 12. More specifically, the output from a TV camera 120, which is mounted on the microscope 35, is fed to a video line generator 122. This video line generator is capable of generating two horizontal and two vertical lines and overlaying them with the incoming video image as the output. The positions of these four lines can be positioned independently and can be calibrated so that they define a rectangular window which indicates where the bonding tip will touch down the top surface of the lead. Output from this video line generator is then displayed on the TV monitor 124.

The invention has been described with reference to specific sources of illumination. Other sources of fluorescent, fiber optic and collimated light sources may be used and are well known within the skill of the art. Also the sequence of adjustments of the light sources may vary.

Having described our invention, what we now claim is:

1. An optical video system for viewing at least two distinct surfaces, said surfaces lying in substantially the same plane, which plane intersects a supporting surface which comprises:
   a first collimated source of illumination forward of the surfaces under investigation, the axis of said illumination lying in a plane substantially normal to said surface, said axis at an angle of 45° to 65° with reference to the supporting surface;
   a second fluorescent source of illumination rearward of the surfaces, the axis of said illumination lying in a plane substantially normal to the surface under investigation, said axis at an angle of 45° to 65° with reference to the supporting surface;
   a third fiber optic source of illumination forward of the surface under investigation, and its axis at an angle of 20° to 40° with reference to both the supporting surface and the plane of the surfaces under investigation, said first, second and third sources defining an area of illumination.

2. The system of claim 1 wherein the surfaces lie in a vertical plane with reference to the plane of the support surface.

3. The system of claim 2 wherein the surface under investigation comprise three distinct surfaces.

4. The system of claim 1 wherein the third source of illumination is at an angle of between 20° to 40° with reference to the plane of the supporting surface and at an angle of 20° to 40° with reference to the plane of the surfaces under investigation.

5. The system of claim 4 wherein said third source comprises first and second sources each said third source being a fiber optic light source.

6. The system of claim 1 wherein the means to view the surfaces under investigation is a stereo microscope.

7. The system of claim 1 wherein the means to view the surfaces under investigation includes a video display system.

8. The system of claim 1 which includes means to bond the surfaces together.

9. The system of claim 1 wherein the axes of illumination intersect at a common point P.

10. The system of claim 9 wherein the surfaces comprise at least one side of a TAB joint, the joint comprising a lead-solder-pad assembly, said joint having a top surface, the point P located at the approximate center of the top surface.

11. The system of claim 10 which includes means to rotate the joint about an axis normal to the supporting surface and passing point P.

12. The system of claim 10 wherein the TAB includes a plurality of joints, the successive joints being spaced apart in parallel relationship and which includes means to move the surfaces of successive joints into the area of illumination.

13. A method for viewing at least two distinct surfaces, said surfaces lying in substantially the same plane, which plane intersects the supporting surface on which the distinct surfaces lie, which includes:
creating a first collimate source of illumination forward of the surface under investigation, the axis of illumination lying in a plane substantially normal to the surface under investigation, said axis at an angle of 25° to 45° with reference to the supporting surface;
creating a second fluorescent source of illumination rearward of the surfaces, the axis of illumination lying in a plane substantially normal to the surface under investigation, said axis at an angle of 45° to 65°;
creating a third fiber optic source of illumination forward of the surfaces under investigation, its axis at an angle of 20° to 40° with reference to both the supporting surface and the surface under investigation;
distinguishing between first and second surfaces by:
aligning the axes of said sources of illumination to define an area of illumination on the surfaces under investigation; and
viewing the illuminated surfaces.

14. The method of claim 13 which includes:
positioning the third source of illumination at an angle of between 30° to 40° with reference to the plane of the supporting surface and at an angle of 20° to 40° with reference to the plane of the surface under investigation.

15. The method of claim 14 wherein said third source of illumination comprises first and second fiber optic sources.

16. The method of claim 13 which includes: displaying visually the surfaces under investigation.

17. The method of claim 1 which includes: bonding said first and second surfaces together.

18. The method of claim 13 which includes: positioning the axes of illumination such that said axes intersect at a common point P.

19. The method of claim 13 which includes:
rotating the joint 180° about a z axis normal to the support surface and which passes through the point P; and
viewing the surfaces of the other side of the joint.

20. The method of claim 13 wherein the TAB includes a plurality of joints said joints said joints being spaced apart in parallel relationship which includes:
moving sequentially the joints of the TAB into the area of illumination.

* * * * *

UNITED STATES PATENT AND TRADEMARK OFFICE
CERTIFICATE OF CORRECTION

PATENT NO. : 4,813,588
DATED : 21 March 1989
INVENTOR(S) : Nilendu Srivastava and Fei-Jain Wu It is certified that error appears in the above—identified patent and that said Letters Patent is hereby corrected as shown below:

On the title page, Item [73] should read

-- [73] Assignee: Micro Robotics Systems Inc.
Chelmsford, Massachusetts --.

Signed and Sealed this

First Day of August, 1989

Attest:

DONALD J. QUIGG

Attesting Officer

Commissioner of Patents and Trademarks